United States Patent [19]

Bonaventura et al.

[11] Patent Number: 5,480,866
[45] Date of Patent: * Jan. 2, 1996

[54] HEMOPROTEINS FOR INHIBITION OF NITRIC OXIDE-MEDIATED HYPOTENSION AND SEPTIC SHOCK

[75] Inventors: Joseph Bonaventura, Beaufort, N.C.; Joseph DeAngelo, Hamtramck, Mich.; Robert G. Kilbourn, Houston, Tex.

[73] Assignees: Duke University; Apex Bioscience, Inc., both of Durham, N.C.; Board of Regents, The University of Texas System, Austin, Tex.

[*] Notice: The portion of the term of this patent subsequent to Mar. 22, 2011, has been disclaimed.

[21] Appl. No.: 184,637

[22] Filed: Jan. 18, 1994

Related U.S. Application Data

[63] Continuation-in-part of Ser. No. 838,603, Feb. 19, 1992, Pat. No. 5,296,466.

[51] Int. Cl.$^6$ ........................................ A61K 38/42
[52] U.S. Cl. ........................... 514/6; 514/12; 514/21; 424/85.2; 530/385
[58] Field of Search ........................... 514/6, 12, 21; 424/85.2; 530/385

[56] References Cited

U.S. PATENT DOCUMENTS

| | | | |
|---|---|---|---|
| 4,061,736 | 12/1977 | Morris et al. | 424/177 |
| 4,584,130 | 4/1986 | Bucci et al. | 260/112 |
| 4,598,064 | 7/1986 | Walder | 514/6 |
| 4,751,068 | 6/1988 | Bickar et al. | 423/437 |
| 5,028,627 | 7/1991 | Kilbourn et al. | 514/565 |
| 5,082,642 | 1/1992 | Bickar et al. | 423/402 |
| 5,296,466 | 3/1994 | Kilbourn et al. | 514/6 |

FOREIGN PATENT DOCUMENTS

| | | |
|---|---|---|
| WO91/04024 | 4/1991 | WIPO . |
| WO91/84023 | 4/1991 | WIPO . |
| WO91/04023 | 4/1991 | WIPO . |
| WO93/00893 | 1/1993 | WIPO . |

OTHER PUBLICATIONS

Bone, Roger C., Annals of Internal Medicine, vol. 115(6), pp. 457–469, 1991.
Glauser, M. P. et al, The Lancet, vol. 338, pp. 732–736, 1991.
Kilbourn, Robert G. et al., Journ. of the National Cancer Institute, vol. 84(11), pp. 827–831, 1992.
Natanson, Charles et al., Annals of Internal Medicine, vol. 120(9), pp. 771–783, 1994.
The Economist, "Panic in the Petri Dish," pp. 61–62, Jul. 23.
Cross, Alan S. et al., Infection and Immunity, vol. 61, No. 7, pp. 2741–2747, Jul. 1993.
Petros, Andy et al., The Lancet, vol. 338, pp. 1557–1558, 1991.
Kilbourn et al., "$N^G$–Methyl–L–arginine Inhibits Tumor Necrosis Factor–Induced Hypotension: Implications for the Involvement of Nitric Oxide," Proc. Natl. Acad. Sci. USA, 87:3629–3632, 1990.
Palmer et al., "Nitric Oxide Release Accounts for the Biological Activity of Endothelium–Derived Relaxing Factor," Nature, 327:524–526, 1987.
Moncada et al., "Generation of Prostacycline and Endothelium–Derived Relaxing Factor from Endothelial Cells," IN: Golles, G., Legran J. Y., and Nurden A. eds., Biology and Pathology of Platelets–Vessel Wall Interactions, pp. 289–304, 1986.
Kilbourn et al., "Activated Macrophages Secrete a Soluble Factor that Inhibits Mitochondrial Respiration of Tumor Cells," The Journal of Immunology, 133(5) :2577–2581, 1984.
Kilbourn & Belloni, "Endothelial Cell Production of Nitrogen Oxides in Response to Interferon γ in Combination with Tumor Necrosis Factor, Interleukin–1, or Endotoxin," Journal of the National Cancer Institute, 82:772–776, 1990.
Aisaka et al., "$N^G$–Methylarginine, an Inhibitor of Endothelium–Derived Nitric Oxide Synthesis, is a Potent Pressor Agent in the Guinea Pig: Does Nitric Oxide Regulate Blood Pressure in Vivo?" Biochemical and Biophysical Research Communications, 160(2) :881–886, 1989.
Vallance et al., "Effects of Endothelium–Derived Nitric Oxide on Peripheral Arteriolar Tone in Man," Lancet, 28:997–999, 1989.
Kilbourn et al., "Reversal of Endotoxin–Mediated Shock by $N^G$–Methyl–L–Arginine, an Inhibitor of Nitric Oxide Synthesis," Biochemical and Biophysical Research Communications, 172(3) :1132–1138, 1990.
Gross et al., "Cytokine–activated Endothelial Cells Express and Isotype of Nitric Oxide Synthase Which is Tetrahydrobiopterin–Dependent. Calmodulin–Independent and Inhibited by Arginine Analogs with a Rank–Order of Potency Characteristic of Activated Macrophages," Biochemical and Biophysical Research Communications, 178(3):823–829, 1991.
Schmidt et al., "Insulin Secretion from Pancreatic B Cells Caused by L–Arginine–Derived Nitrogen Oxides," Science, 255:721–723, 1992.
Sakuma et al., "Identification of Arginine as a Precursor of Endothelium–Derived Relaxing Factor," Proc. Natl. Acad. Sci. USA, 85:8664–8667, 1988.
Stuehr & Marletta, "Induction of Nitrite/Nitrate Synthesis in Murine Macrophages by BCG Infections, Lymphokines, or (List continued on next page.)

Primary Examiner—Michael G. Wityshyn
Assistant Examiner—C. Sayala
Attorney, Agent, or Firm—Arnold, White & Durkee

[57] ABSTRACT

The invention is directed to a method for the prophylaxis or treatment of an animal for deleterious physiological effects such as systemic hypotension caused by nitric oxide production induced by a biological response modifier. Examples of such biological response modifiers include but are not limited to a cytokine and an endotoxin. The invention is also directed to a method for the treatment of septic shock. Hemoproteins such as hemoglobin, myoglobin, hemalbumin and methemalbumin, for example, are useful when administered to a hypotensive patient.

14 Claims, 3 Drawing Sheets

OTHER PUBLICATIONS

Interferon-γ," *The Journal of Immunology,* 139(2):518–525, 1987.

Bone, Roger C. "The Pathogenesis of Sepsis," *Ann. Int. Med.* 115:457–469, 1991.

Bone, Roger C. "A Critical Evaluation of New Agents for the Treatment of Sepsis," *JAMA* 266(12):1686–1691, 1991.

Glauser, M. P., et al. "Septic Shock: Pathogenesis," *The Lancet,* 338:732–736, 1991.

Johnston, J. "Molecular Science Sets Its Sights on Septic Shock," *J. NIH Res.* 3:61–65, 1991.

Moncada, S. and E. A. Higgs, "Endogenous Nitric Oxide: Physiology, Pathology, and Clinical Relevance," *Eur. J. Clin. Invest.* 21:361–374, 1991.

Moncada, S., et al. "The L–Arginine: Nitric Oxide Pathway," *J. Cardiovascular Pharm.* 7(Suppl. 3):S1–S9, 1991.

Moncada, S., et al. "Nitric Oxide: Physiology, Pathophysiology, and Pharmacology," *Pharmacological Reviews* 43(2):109–142.

Parratt, J. R., and J. C. Stoclet, "Possible Role of Nitric Oxide in Refractory Hypotension Associated with Sepsis and Endotoxaemia and with Multiple Organ Failure," *Applied Cardiopulmonary Pathophysiology* 4:143–149, 1991.

Snell, R. J., and J. E. Parrillo, "Cardiovascular Dysfunction in Septic Shock," *Chest* 99(4):1000–1009, 1991.

Wang, Q., et al. "Nitric Oxide Hemoglobin in Mice and Rats in Endotoxic Shock," *Life Sciences* 49:PL–55–60, 1991.

Bickar et al., "Carbon Monoxide–Driven Reduction of Ferric Heme and Heme Proteins," *Journal of Biological Chemistry,* 259(17):10777–10783, 1984.

Martin et al,. "Selective Blockade of Endothelium–Dependent and Glyceryl Trinitrate–Induced Relaxation by Hemoglobin and by Methylene Blue in the Rabbit Aorta," *The Journal of Pharmacology and Experimental Therapeutics,* 232(3):708–716, 1985.

Buga et al., "Endothelium–Derived Nitric Oxide Relaxes Nonvascular Smooth Muscle," *European Journal of Pharmacology,* 161:61–72, 1989.

Stuehr et al., "Activated Murine Macrophages Secrete a Metabolite of Arginine with the Bioactivity of Endothelium–Derived Relaxing Factor and the Chemical Reactivity of Nitric Oxide," *J. Exp. Med.,* 169:1011–1020, 1989.

Stuehr et al., "Synthesis of Nitrogen Oxides from L–Arginine by Macrophage Cytosol: Requirement for Inducible and Constitutive Components," *Biochemical and Biophysical Research Communications,* 161(2):420–426, 1989.

Torti et al., "A Macrophage Factor Inhibits Adipocyte Gene Expression: An in Vitro Model of Cachexia," *Science,* 229:867–871, 1985.

Palmer et al., "Vascular Endothelial Cells Synthesize Nitric Oxide from L–Arginine," *Nature,* 333:664–666, 1988.

Old, Lloyd J., "Tumor Necrosis Factor (TNF)," 230:630–632, 1985.

Yoshida and Kasama, "Biotransformation of Nitric Oxide," *Environmental Health Perspectives,* 73:201–206, 1987.

Schmidt et al., "Arginine is a Physiological Precursor of Endothelium–Derived Nitric Oxide," *European Journal of Pharmacology,* 154:213–216, 1988.

Reif and Simmons, "Nitric Oxide Mediates Iron Release from Ferritin," *Archives of Biochemistry and Biophysics,* 283(2):537–541, 1990.

Kruszyna et al., "Nitrite Conversion to Nitric Oxide in Red Cells and Its Stabilization as a Nitrosylated Valency Hybrid of Hemoglobin," *The Journal of Pharmacology and Experimental Therapeutics,* 241(1):307–313, 1987.

Kosaka et al., "The Interaction Between Nitrogen Oxides and Hemoglobin and Endothelium–Derived Relaxing Factor," *Free Radical Biology and Medicine,* 7:653–658, 1989.

Chevion et al., "Iron–Nitrosyl Bond configuration in Nitrosyl–Hemoproteins: A Comparative EPR Study of Hemoglobin A and Hemoglobin Kansas," *Israel Journal of Chemistry,* 15:311–317, 1976.

Collier and Vallance, "Second Messenger Role for NO Widens to Nervous and Immune Systems," *Trends in Pharmacological Sciences Including Toxicological Sciences,* Elseview Science Publishers, Ltd., front page and pp. 428–431, 1989.

Ignarro et al., "Endothelium–Derived Relaxing Factor Produced and Released from Artery and Vein is Nitric Oxide," *Proc. Natl. Acad. Sci. USA,* 84:9265–9269, 1987.

Murray et al., "Stabilization and Partial Characterization of Endothelium–Derived Relaxing Factor from Cultured Bovine Aortic Endothelial Cells," *Biochemical and Biophysical Research Communications,* 141(2):689–696, 1986.

Marletta, Michael A., "Nitric Oxide: Biosynthesis and Biological Significance," name of publication unknown, Elseview Science Publishers, Ltd., pp. 448–493, 1989.

Geokas et al., "Methamalbumin in the Diagnosis of Acute Hemorrhagic Pancreatitis,", *Annals of Internal Medicine,* 81:483–486, 1974.

Murray et al., "Measurement of Methaemalbumin in Plasma," *J. Clin. Path.,* 26:446–447, 1973.

Muller–Eberhard and Morgan, "Porphyrin–Binding Proteins in Serum," *Annals New York Academy of Sciences,* 224:624–649, 1975.

Baur, Ernst W., "The Evolution of Methaemalbumin," *Comp. Biochem. Physiol.,* 30:657–664, 1969.

Chong et al., "Determination of Methaemalbumin in Plasma," *J. Clinical Pathology,* 20:211–212, 1967.

Marden et al., "Flash Photolysis of the Serum Albumin–Heme–CO Complex," *Biochemistry,* 28(10):4422–4426, 1989.

Bonkovsky et al., "Intravenous Heme–Albumin in Acute Intermittent Prophyria: Evidence for Repletion of Depatic Hemoproteins and Regulatory Heme Pools," *The American Journal of Gastroenterology,* 86(8):1050–1056, 1991.

Wang et al., "Nitric Oxide Hemoglobin in Mice and Rats in Endotoxic Shock" *Life Sciences,* 49:PL55–PL60, 1991.Westenberger et al., "Formation of Free Radicals and Nitric Oxide Derivative of Hemoglobin in Rats During Shock Syndrome", *Free Radical Res. Commun.,* 11:167–178, 1990.

Kosaka et al., "Detection of Nitric Oxide Production in Lipopolysaccharide–Treated Rats by ESR Using Carbon Monoxide Hemoglobin", *Biochem. and Biophys. Res. Commun.,* 184(2):1119–1124, 1992.

Stamler et al., "Biochemistry of Nitric Oxide and Its Redox–Activated Forms" *Science,* 258:1898–1902, 1992.

Koshland, Jr., "Editorial–The Molecule of the Year", *Science,* 258:1861, 1992.

Culotta et al., "NO News Is Good News", *Science,* 258:1862–1865, 1992.

Wang et al., Nitric Oxide Hemoglobin in Mice and Rats in Endotoxic Shock, *Chemical Abstracts,* 115(15):659m, col.

1, issued 1991, Oct. 14, abstract–no. 156 199a, *Life Sci.*, 49(11) :PL55–PL60, 1991.

Westenberger et al., Formation of Free Radicals and Nitric Oxide Derivative of Hemoglobin in Rats During Shock Syndrome, *Chemical Abstracts*, 114(21) :597, col. 2; 598, col. 1, issued May 27, 1991, abstract–no. 204 845m, *Free Radical Res. Commun.*, 11(1–3) :167–178, 1990.

Gruetter et al., "Coronary Arterial Relaxation and Guanylate Cyclase Activation by Cigarette Smoke, N'–Nitrosonornicotine and Nitric Oxide," *The Journal of Pharmacology and Experimental Therapeutics*, 214(1) :9–15, 1980.

HEMOPROTEINS FOR INHIBITION OF NITRIC OXIDE-MEDIATED HYPOTENSION AND SEPTIC SHOCK

This application is a continuation-in-part of U.S. Ser. No. 07/838,603, filed Feb. 19, 1992, now U.S. Pat. No. 5,296,466, which is incorporated by reference herein.

FIELD OF THE INVENTION

The invention is directed to a method for the prophylaxis or treatment of an animal for systemic hypotension induced by a biological response modifier. Examples of such biological response modifiers include but are not limited to a cytokine and an endotoxin. The invention is also directed to a method for the treatment of septic shock.

BACKGROUND OF THE INVENTION

Endothelium-Derived Relaxing Factor

Endothelial cells have been shown to produce a potent vasodilator known as Endothelium-Derived Relaxing Factor (EDRF). Many naturally occurring substances which act as physiological vasodilators mediate all or part of their action by stimulating the release of EDRF. Examples of such substances include acetylcholine, histamine, bradykinin, leukotrienes, ADP, and ATP. Recent studies have identified EDRF as nitric oxide, a short lived, unstable compound (Ignarro et al., 1987, Proc. Natl. Acad. Sci. U.S.A. 84:9265–9269 and Palmer et al., 1987, Nature 327:524–526).

L-Arginine is the metabolic precursor of EDRF (Schmidt et al., 1988, Eur. J. Pharmacol. 154:213–216). $N^G$-methyl-L-arginine is a competitive inhibitor of the biosynthetic pathway of EDRF (Palmer et al., 1988, Nature 333:664–666). Administration of $N^G$-methyl-L-arginine to guinea pigs and rabbits has been shown to increase blood pressure (Aisaka et al., 1989, Biochem. Biophys. Res. Commun. 160:881–886). Nitric oxide (NO) appears to be synthesized from L-arginine by the enzyme, NO synthase; the coproduct is L-citrulline (Moncada et al., 1991, J. Cardiovascular Pharmacol. 17 (Suppl. 3):S1–S9). NO is an endogenous stimulator for soluble guanylate cyclase.

Nitric oxide has been found to be produced by macrophages, endothelial cells, neutrophils, Kupffer cells and hepatocytes, murine fibroblasts stimulated with cytokines, and EMT-6 cells, a spontaneous murine mammary adenocarcinoma cell line when treated with cytokine (reviewed in Moncada et al., 1991, Pharmacol. Reviews 43:109–142). Specifically, macrophage cells become activated by 12–36 hour treatments with gamma-interferon, bacterial endotoxin and various cytokines (reviewed in Collier and Vallance, 1989, Trends in Pharmacol. Sci. 10:427–431).

Endothelial cells in the presence of gamma-interferon, have been found to secrete large quantities of arginine-derived nitrogen oxides after activation by tumor necrosis factor (TNF) or endotoxin (Kilbourn and Belloni, 1990, J. Natl. Cancer Inst. 82:772–776). TNF causes marked hypotension in mammals (Tracey et al., 1986, Gynecol. Obstet. 164:415–422; Old, 1985, Science 230:630–632). Additionally, TNF is thought to mediate the vascular collapse resulting from bacterial endotoxin (Beutler et al., 1985, Science 229:869–871). It has recently been shown that arginine derivatives inhibit systemic hypotension associated with nitric oxide production, specifically treatment with TNF, gamma interferon, interleukin-2, and bacterial endotoxin (Kilbourn et al., U.S. Pat. No. 5,028,627, issued Jul. 2, 1991; PCT Application no. WO 91/04023, published Apr. 4, 1991; and Kilbourn et al., 1990, Proc. Natl. Acad. Sci. U.S.A. 87:3629–3632). Nitric oxide overproduction is also thought to be involved in numerous other pathogenic or potentially pathogenic syndromes. For example, some of these syndromes are thought to be associated with malaria, senescence and diabetes. The procedures of the present invention may also be used to prevent, inhibit and/or alleviate such NO-related syndromes.

Interaction of Hemoglobin with Endothelium-Derived Relaxation Factor

Nitric oxide reacts with hemoglobin to form nitrosylhemoglobin (Kosaka et al., 1989, Free Radical Biology 7:653–658). Nitrosylhemoglobin reacts with oxygen to yield nitrate and methemoglobin, which is rapidly reduced by methemoglobin reductase. At least part of the nitric oxide is oxidized by oxygen to $NO_2$, which is in turn converted to nitrite and nitrate.

The formation of nitrosylhemoglobin has been used to quantify nitric oxide present in mice given bacterial endotoxin, specifically by using electron paramagnetic resonance (EPR) spectroscopy to detect NO liganded to hemoglobin (Wang et al., 1991, Life Sciences 49:55–60). Although bacterial endotoxin induces septic shock, hypotension was not observed in the Wang et al. study. Those skilled in the art recognize that such EPR studies may be used to quantitate the binding of NO to other hemoproteins as well.

Hemoglobin has also been found to inhibit nonvascular relaxant responses to EDRF (Buga et al., 1989, Eur. J. Pharmacol. 161:61–72). Furthermore, hemoglobin at 1 µM reduced and at 10 µM abolished the endothelium-dependent relaxation induced by acetylcholine or by A23187 in rabbit aortic rings (Martin et al., 1985, J. Pharmacol. Exp. Ther. 232:708–716). It was hypothesized by Martin et al. that the hemoglobin inhibits endothelium-dependent induced relaxation by binding nitric oxide.

Septic Shock

Septic shock is characterized by inadequate tissue perfusion and is usually caused by gram-negative enteric bacilli such as Escherichia coli, Klebsiella, Enterobacter, Pseudomonas, Serratia, and Bacteroides (see Harrison's INTERNAL MEDICINE, 10th Ed., vol. 1, Petersdorf et al., eds., McGraw Hill, N.Y. 1983). Gram-negative bacilli possess endotoxin, also known as lipopolysaccharide (LPS), which is a cell-wall component that can activate leukocytes in minute amounts in the blood.

Septic shock is characterized by chills, fever, nausea, vomiting, diarrhea, and prostration. The subsequent development of septic shock is characterized by tachycardia, tachypnea, hypotension, peripheral cyanosis, mental obtundation, and oliguria. As shock progresses, oliguria persists, and heart failure, respiratory insufficiency, and coma supervene. Death usually results from pulmonary edema, generalized anoxemia secondary to respiratory insufficiency, cardiac arrhythmia, disseminated intravascular coagulation with bleeding, cerebral anoxia, or a combination of the above.

Most of the damage caused by septic shock is thought to be caused by endotoxin. It has also been hypothesized that nitric oxide plays a major role in effecting hypotension in those exposed to endotoxin (Kilbourn et al. Biochem. and Biophys. Res. Comm. 1990, vol. 172:1132–1138). Studies have shown that the hypotension and loss of vascular responsiveness resulting from endotoxin administration is reversed by the administration of analogues of L-arginine which inhibit nitric oxide production (Parratt and Stoclet, 1991, *Applied Cardiopulmonary Pathophysiology* 4:143–149; and Kilbourn et al., 1990, *Proc. Natl. Acad. Sci. U.S.A.* 87:3629–3632).

In certain cases, acute blood loss may cause hypotension. After initial recovery due to standard hypotension treatment, a breach of intestinal integrity may subsequently cause septic hypotension. Such a syndrome is readily treated according to the methods of the present invention.

Treatments for Septic Shock

There are currently a number of clinical procedures available for the treatment of septic shock (reviewed in Harrison's INTERNAL MEDICINE, 10th Ed., vol.1, Petersdorf et al., eds., McGraw Hill, N.Y. 1983). However each has its drawbacks. One treatment involves the replacement of blood volume with blood, plasma, or other fluids such as human serum albumin in appropriate electrolyte solutions such as dextrose saline and bicarbonate. However, large quantities of these substances are required and may amount to 8 to 12 liters in only a few hours, leading to massive shifts in fluid and electrolyte balances.

Antibiotics may also be used to treat septic shock. However, to determine the appropriate antibiotics to use, blood cultures must be taken and evaluated. Such cultures take time. Additionally, antibiotics may initially worsen shock caused by bacteria since they kill the bacteria and the dying organisms can release even more lipopolysaccharide into the body.

Vasoactive drugs such as beta-receptor stimulants (e.g. isoproterenol and dopamine) and alpha-receptor blocking agents (phenoxybenzamine and phentolamine) have also been therapeutically used since septic shock is accompanied by maximal stimulation of alpha-adrenergic receptors. However, all of these drugs may have serious side effects. In addition, studies by Stoclet et al. (*Amer. J. Physiol.* 259:H1038–1043) suggest that endotoxic shock and NO production can cause lowered sensitivity to these agents, decreasing their effectiveness. The iron hemoprotein therapy of the present invention may be used to reverse this loss of sensitivity.

Another treatment approach involves using human antiserum to *E. coli* J5, a mutant strain that produces endotoxin without the variable oligosaccharide side chains. However, since such antiserum comes from many different human donors with varying immune responses to the antigen, it cannot be rigidly standardized for effectiveness. Such antiserum may also transmit infectious agents. To circumvent these problems, monoclonal antibodies that bind to endotoxin are currently being tested in patients suffering from septic shock (reviewed in Johnston, 1991, *J. NIH Res.* 3:61–65). A disadvantage of this approach is that treatment of septic patients with antiendotoxin antibodies has no immediate effect on blood pressure and may not work at all if patients are not treated at an early stage.

Another approach used to treat septic shock involves administering bactericidal permeability-increasing protein (BPI), a human protein derived from neutrophil granules. This protein binds to LPS. Versions of the molecule are currently being developed (reviewed in Johnston, 1991, *J. NIH Res.* 3:61–65).

Approaches are also being developed for treating septic shock by preventing endotoxin from activating leukocytes that start the inflammatory response (reviewed in Johnston, 1991, *J. NIH Res.* 3:61–65). Examples of such approaches include administering a soluble interleukin-1 (IL-1) receptor, an IL-1 receptor antagonist, a monoclonal antibody to TNF-α, soluble TNF receptor and a monoclonal antibody to TNF-α receptor. All of these approaches suffer from the fact that blockade of the cytokine receptor interaction does not have an immediate effect on nitric oxide production by NO synthase (i.e.—once induced by cytokines, NO synthase continues to produce NO even after removal of the stimulus).

The present invention involves the treatment of a nitric oxide-induced malady such as hypotension by administration of a metal-containing hemoprotein which has substantial affinity for nitric oxide and/or catalyzes nitric oxide oxidation to nitrates or nitrites. Iron is a preferred metal, although other transition metals such as nickel, ruthenium, cobalt or copper may be bound to heme and be nitric oxide-reactive. One preferred hemoprotein is hemoglobin, particularly recombinant hemoglobin. Another preferred hemoprotein is hemalbumin. Myoglobin, which also is known to bind nitric oxide, may also be utilized. Additional iron hemoproteins, including peroxidase, catalase, cytochrome oxidase and certain cytochromes, such as cytochrome P-450, are known and may be used to demonstrate the above mentioned nitric oxide-related effects. Particularly preferred hemoglobins are those which have a long circulating lifetime, e.g., those which have a poor affinity for haptoglobin. Those skilled in the art will recognize that other iron heme-containing proteins or peptides binding NO may be administered to an animal in a pharmaceutically effective amount to remove nitric oxide and prevent or treat hypotension or other NO-induced deleterious effects.

Despite previous results showing the interaction of iron hemoproteins such as hemoglobin with nitric oxide, the therapeutically effective results of the present inventive method are quite surprising and unexpected. Such a result could not have been expected in view of the fact that normal mammalian blood fluid is replete with hemoglobin contained in red blood cells which contain about 34% hemoglobin. Such cells usually constitute over 43% of the blood. Thus blood is about 15% hemoglobin. Additionally, nitric oxide is quite lipophilic and readily penetrates red blood cells. One skilled in the art would have expected that any effects of a free iron hemoprotein such as hemoglobin in the blood to remove deleterious nitric oxide would have been insignificant as compared to the effects of preexisting hemoglobin contained in red blood cells. The basis for the surprising and unexpectedly effective results of the present invention are incompletely understood at the present time, but, as the present invention is described, it will be clear to those of skill in the art that the free hemoproteins of the present invention such as hemoprotein are phenomenally effective for therapeutic purposes related to a reversal of deleterious physiological effects induced by nitric oxide in vivo. Hemalbumin, not binding haptoglobin and having very favorable in vivo circulatory characteristics, is particularly valuable.

SUMMARY OF THE INVENTION

The invention is directed to a method for the prophylaxis or treatment of an animal for systemic hypotension or other pathogenic syndromes induced by inappropriate nitric oxide production. Such hypotension may be induced by certain cytokines or a microbial toxin such as bacterial endotoxin. The method involves administering a therapeutically effective amount of a metal hemoprotein such as hemalbumin or the like. The administration is preferably intravascular, which includes intraarterial and intravenous. Other parenteral administration routes, e.g. peritoneal or intralymphatic, to name but a few, can be used for removal of undesired NO production at related sites. Enteral administration could be feasible if the hemoprotein or a derivative thereof was resistant to digestion and passed into the circulation. The animal may be, for example, a domestic mammal or a human patient. The systemic hypotension most characteristically results from abnormal production of nitric oxide induced by a cytokine or microbial toxin. A therapeutically effective amount of iron hemoprotein is an amount sufficient to bind and/or oxidize substantially all of the free nitric oxide and thus removing it from the circulation. In a preferred embodiment, the iron hemoprotein is hemalbumin and is administered intravascularly.

Bacterial endotoxin is a primary causative agent of septic shock. Elevated levels of nitric oxide have been found in animals in septic shock (Wang et al., 1991, *Life Sciences* 49:55–60). Therefore, the invention is also directed to a method for the treatment of septic shock in a patient comprising administering a therapeutically effective amount of an iron hemoprotein such as the preferred hemalbumin.

DETAILED DESCRIPTION OF THE INVENTION

In a major embodiment, the present invention is directed to a method for the prophylaxis or treatment of an animal for systemic hypotension induced by a biological response modifier directly or indirectly causing nitric oxide overproduction. Examples of such biological response modifiers include but are not limited to cytokines. The invention is also directed to a method for the treatment of septic shock and associated hypotension.

Prophylaxis or treatment involves parenterally administering hemoprotein at from about 0.1 to about 10 g/kg body weight. The therapeutic models exemplified herein serve also as prophylactic examples, the hemoprotein being administered prior to pervasion of the nitric oxide inducer. While prophylaxis of septic shock will be unusual, as septic shock is never planned, cytokine therapy is planned and attendant nitric-oxide-induced hypotension may be prevented or inhibited by prior hemoprotein administration.

Preparation of Hemoglobin

The starting material, unmodified hemoglobin, may be obtained using procedures known in the art (see for example, PCT Application Publication No. WO 88/03408, published May 19, 1988; U.S. Pat. No. 4,001,401; Feola et el., 1983, *Surgery Gynecology and Obstetrics* 157:399–408; De Venuto et el., 1979, Surgery Gynecology and Obstetrics 149:417–436). For example, unmodified stroma-free hemoglobin may be obtained as follows: (a) obtaining whole blood; (b) separating red blood cells from other components of whole blood; (c) isolating the hemoglobin from the erythrocytes; and (d) separating the hemoglobin from stroma and other impurities.

Stroma-free hemoglobin can be prepared by starting with erythrocytes in freshly drawn, outdated, or frozen packed cells or whole blood. The blood should be drawn in a sterile fashion into containers with sufficient anticoagulant activity to prevent clot formation.

In one embodiment, blood cells are washed in a saline solution and centrifuged to separate red blood cells from white blood cells as well as to additionally remove free proteins (Feola et al., 1983, *Surgery Gynecology and Obstetrics* 157:399–408). In another embodiment, the red cells may be separated from other blood cells by passing through a semi-continuous type centrifuge as described in PCT Application Publication No. WO 88/03408, published May 19, 1988.

Hemoglobin may be isolated in one embodiment by diluting the red blood cell solution in water or an organic solvent at 2°–10° C. to separate the hemoglobin in red blood cells from all cell debris (PCT Application Publication No. WO 88/03408, published May 19, 1988; U.S. Pat. No. 4,001,401; Feola et al., 1983, *Surgery Gynecology and Obstetrics* 157:399–408). In another embodiment, the hemoglobin is precipitated as a zinc complex by the addition of a zinc salt to a hemoglobin solution (De Venuto et al., 1979, Surgery Gynecology and Obstetrics 149:417–436).

The isolated hemoglobin, in another embodiment, may be purified by ultrafiltration through for example a 0.5 micron filter which retains the cellular components and passes the hemoglobin.

Hemoglobin may also be obtained through other procedures known in the art. For example, bacterial strains (see for example Nagai and Hoffman, U.S. Pat. No. 5,028,588, issued Jul. 2, 1991) or yeast (see for example PCT Application Publication No. WO90/13645, published Nov. 15, 1990), or other eukaryotic organisms may be engineered to produce hemoglobin by recombinant DNA techniques. Recombinant hemoglobin is thought to be particularly advantageous because it can be readily produced in large quantities and because utilization of such recombinant hemoglobin obviates the possibility of blood-borne infection such as that by various viruses or retroviruses.

The hemoglobin may be for example, any human hemoglobin, including but not limited to HbA (alpha$_2$beta$_2$), HbA2 (alpha$_2$delta$_2$), HbF (alpha$_2$gamma$_2$), Hb Barts (gamma4), HbH (beta$_4$), and Hb Portland I (zeta$_2$gamma$_2$), Hb Portland II (zeta$_2$beta$_2$), Hb Portland III (zeta$_2$delta$_2$) Hb Gower I (zeta$_2$epsilon$_2$), and Hb Gower II (alpha$_2$epsilon$_2$); as well as any other animal hemoglobin, e.g. bovine or porcine hemoglobin.

The hemoglobin used in the method of the present invention may be chemically modified using procedures known in the art to increase tetramer stability and/or lower oxygen affinity. Examples of chemical modifications to increase the tetramer stability include but are not limited to crosslinking with polyalkylene glycol (Iwashita, U.S. Pat. No. 4,412,989 and 4,301,144), with polyalkylene oxide (Iwasake, U.S. Pat. No. 4,670,417); with a polysaccharide (Nicolau, U.S. Pat. Nos. 4,321,259 and 4,473,563); with inositol phosphate (Wong, U.S. Pat. Nos. 4,710,488 and 4,650,786); with a bifunctional crosslinking agent (Morris et al., U.S. Pat. No. 4,061,736); with insulin (Ajisaka, U.S. Pat. No. 4,377,512); and with a crosslinking agent so that the hemoglobin composition is intramolecularly crosslinked between lys 99 alpha$_1$ and lys 99 alpha$_2$ (Walder, U.S. Pat. No. 4,598,064). Examples of chemical modifications to decrease the oxygen affinity of isolated hemoglobin include but are not limited to polymerization with pyridoxal phosphate (Sehgal et al., 1984, *Surgery*, 95:433–438) and using reagents that mimic 2,3-DPG (Bucci et al., U.S. Pat. No. 4,584,130).

In a further embodiment, the hemoglobin used in the method of the present invention may be a hemoglobin variant, a hemoglobin comprising a globin chain from a nucleotide sequence which has been altered in such a fashion so as to result in the alteration of the structure or function of the hemoglobin, but so that the hemoglobin still remains functionally active as defined by the ability to reversibly bind to oxygen (or nitric oxide, of course). Categories of hemoglobin variants include but are not limited to variants which autopolymerize; variants in which the tetramer does not dissociate under physiological conditions in vivo (e.g. Hb Rainier, beta-145 tyrosine is replaced by cysteine); variants with lowered intrinsic oxygen affinity, i.e. a hemoglobin having a P50 of at least about 10 mm Hg under physiological conditions (e.g. Hb Chico, beta-66 lysine is replaced by threonine; Hb Raleigh, beta-1 valine is replaced by alanine; Hb Titusville, alpha-94 aspartate to asparagine; Hb Beth Israel (beta-102 asparagine is replaced with serine; and Hb Kansas, beta-102 asparagine to threonine; variants that are stable in alkali (e.g. Motown/Hacettepe, beta-127 or glutamine is replaced with glutamic acid); variants that are stable in acid; variants which have a lowered binding affinity to haptoglobin; variants with an increase intrinsic oxygen affinity, i.e. a hemoglobin having a P50of at most about 1 mm Hg under physiological conditions (e.g. HbA Deer Lodge, beta-2 histidine is replaced with arginine, Labossiere et al., 1972, *Clin. Biochem.* 5:46–50; HbA Abruzzo, beta-143 histidine is replaced with arginine, Tentori et al., 1972, *Clin. Chim. Acta* 38:258–262; and HbA McKees Rocks, beta-145 tyrosine is replaced with a termination sequence, Winslow et al., 1976, *J. Clin. Invest.* 57:772–781).

Acid stable hemoglobin variants may include those that replace the histidine at the alpha-103 position with an amino acid is not ionized in acid (Perutz, 1974, *Nature* 247:341). Examples of such amino acids include serine, threonine, leucine, and alanine.

Haptoglobin nonbinding hemoglobin variants are those with variation in the alpha-121-127 sequence. This sequence has been shown to be involved in the binding of haptoglobin which is believed incident to increased circulatory clearance (McCormick and Atorssi, 1990, *J. Prot. Chem.* 9:735).

The globin variants may be produced by various methods known in the art. The manipulations which result in their production can occur at the gene or protein level. The globin may be altered at the gene level by site-specific mutagenesis using well-known procedures. One approach which may be taken involves the use of synthetic oligonucleotides to construct variant globins with base substitutions. In one embodiment, a short oligonucleotide containing the mutation is synthesized and annealed to the single-stranded form of the wild-type globin gene (Zoller and Smith, 1984, *DNA* 3:479–488). The resulting short heteroduplex can serve as primer for second strand synthesis by DNA polymerase. At the 5' end, a single stranded nick is formed which is closed by DNA ligase. In another embodiment, two complementary oligonucleotides are synthesized, each containing the mutant sequence. The duplex that forms after annealing these complementary oligonucleotides, can be joined to a larger DNA molecule by DNA ligase provided that the ends of both molecules have complementary single-stranded "sticky" ends. Another approach which may be taken involves introducing a small single-stranded gap in the DNA molecule followed by mis-repair DNA synthesis i.e., the misincorporation of a non-complementary nucleotide in the gap (Botstein and Shortle, 1985, *Science* 229:1193). The incorporation of a thiol nucleotide into the gap may minimize the excision of the non-complementary nucleotide. Alternatively, a globin variant may be prepared by chemically synthesizing the DNA encoding the globin variant using procedures known in the art (see for example Froehler, 1986, *Nucl. Acids Res.* 14:5399–5407 and Caruthers et al., 1982, GENETIC ENGINEERING, J. K. Setlow and A. Hollaender eds., Plenum Press, New York, vol. 4, pp. 1–17). In a preferred embodiment, fragments of the variant globin-coding nucleic acid sequence are chemically synthesized and these fragments are subsequently ligated together. The resulting variant globin-coding strands may be amplified using procedures known in the art, e.g. PCR technology, and subsequently inserted into a cloning vector as described in, e.g., PCT Application Publication No. WO90/13645, published Nov. 15, 1990). In specific embodiments, site-specific mutants may be created by introducing mismatches into the oligonucleotides used to prime the PCR amplification (Jones and Howard, 1990, *Biotechniques* 8:178–180).

Manipulations of the globin sequence may be carried out at the protein level. Any of numerous chemical modifications may be carried out by known techniques including but not limited to specific chemical cleavage by cyanogen bromide, trypsin, chymotrypsin, papain, or V8 protease, $NaBH_4$ acetylation, formylation, oxidation, reduction; etc. Alternatively, the variant globin protein may be chemically synthesized using procedures known in the art, such as commercially available peptide synthesizers and the like. Such standard techniques of polypeptide synthesis can be found described in such publications as Merrifield, 1963, *J. Chem. Soc.* 85:2149–2154 and Hunkapillar et al., 1984, Nature (London) 310:105–111). Analogous alterations may be made for the albumin component of the preferred hemalbumin.

Treatment of Hypotension and Septic Shock with Hemoprotein

The hemoglobin prepared according to the procedures described above may be used for the prophylaxis or treatment of systemic hypotension or septic shock induced by internal nitric oxide production. Such internal nitric oxide production may result from the treatment of an animal with a cytokine which includes but is not limited to tumor necrosis factor, interleukin-1, and interleukin-2, in the case of systemic hypotension. In a specific embodiment, hemoglobin may be used for prophylaxis or treatment of systemic hypotension in a patient induced by chemotherapeutic treatment with such cytokines. In septic shock, the production of nitric oxide results from the exposure of an animal to a bacterial endotoxin. Viral, fungal or enterotoxin-producing bacteria may also be found to directly or indirectly induce NO overproduction alleviatable by administration of the hemoproteins of the present invention.

Hemalbumin, the preferred iron hemoprotein used in the present invention, is mixed with a pharmaceutically acceptable carrier. The pharmaceutical carriers are physiologically compatible buffers as Hank's or Ringer's solution, physiological saline, a mixture consisting of saline and glucose, heparinized sodium-citrate-citric acid-dextrose solution, and the like. The hemalbumin for use in the methods of the present invention can be mixed with colloidal-like plasma substitutes and plasma expanders such as linear polysaccharides (e.g. dextran), hydroxyethyl starch, balanced fluid gelatin, and other plasma proteins. Additionally, the hemalbumin may be mixed with water soluble and physiologically acceptable polymeric plasma substitutes, examples of which include polyvinyl alcohol, poly(ethylene oxide), polyvinylpyrrolidone, and ethylene oxide-polypropylene glycol condensates and the like.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions an also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Techniques and formulations suitable for administering the compositions comprising iron hemoprotein generally may be found in *Remington's Pharmaceutical Sciences*, Meade Publishing Col., Easton, Pa., latest edition. In a preferred embodiment, the hemalbumin is administered intravascularly. The amount of iron hemoprotein administered, the effective amount, is an amount sufficient to bind substantially all of the nitric oxide present, thus removing free nitric oxide from circulation. Such an effective amount is generally in a range of from about 0.1 g/kg body weight to about 10 g/kg body weight.

The following examples are presented to illustrate a best mode and preferred embodiments of the present invention and are not meant to limit the claimed invention unless otherwise specified.

EXAMPLE 1

Abrogation of Blood Pressure Decline

Experiments were carried out on conditioned mongrel dogs weighing 23–28 kg. Animal care was in accordance with the recommendations of the American Association for Accreditation of Laboratory Animal Care and met all standards prescribed by the *Guide for the Care and Use of Laboratory Animals* (Committee on Care and Use of Laboratory Animals (1978) *Guide for the Care and Use of Laboratory Animals* (Natl. Inst. Health, Bethesda, Md.) DHEW Publ. No. (NIH) 78–83.

The dog was fasted overnight before the day of the experiment and was anesthetized with pentobarbital (25 mg/kg, i.v.), orotracheally intubated and ventilated with a Harvard pump at a nominal rate of 12 breaths per minute and a tidal volume of 15 ml/kg. The dog was instrumented with a cordis for the introduction of a Swan-ganz catheter for measurement of central venous and pulmonary arterial pressures as well as an arterial line for continuous blood pressure monitoring via a computer driven analog to digital processor.

After the blood pressure and heart rate was stabilized, endotoxin was administered to the dog as a bolus injection (50 µg/kg, i.v. in 10 ml DPBS. After the onset of hypotension, a rapid infusion of 50 ml hemoglobin (5.0 g commercially available bovine hemoglobin/100 ml) over 20 seconds was administered by a central venous catheter. Cardiovascular changes were monitored for an additional 5 hrs. after hemoglobin administration.

Figure 1:
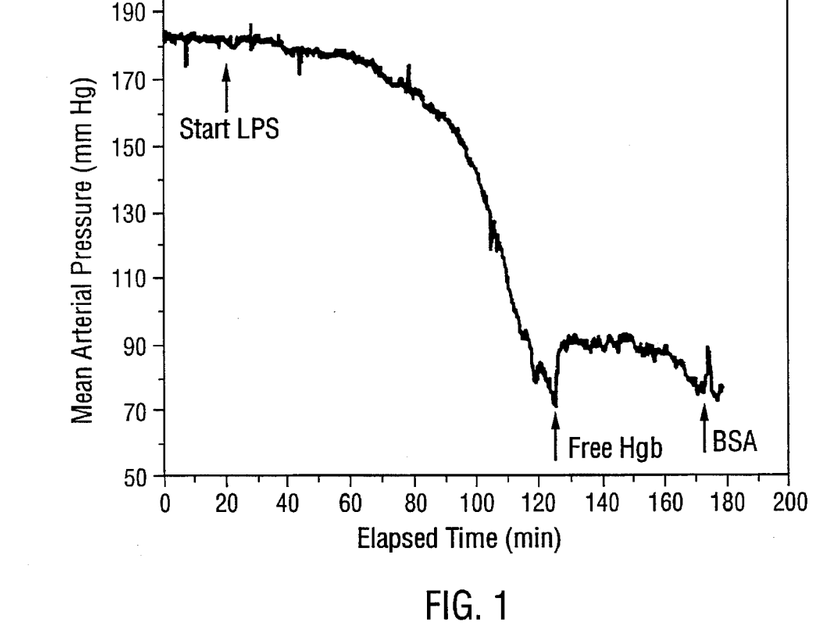
FIG. 1 shows the effect of hemoglobin on endotoxin-induced hypotension in a dog. The endotoxin-induced mean arterial decline is interrupted by administration of hemoglobin.

A tracing depicting endotoxin-induced hypotension, its inhibition by hemoglobin, and subsequent administration of bovine serum albumin (5 grams) is shown in FIG. 1. Mean arterial blood pressure declined from 160 mm Hg to 70 mm Hg two hours after endotoxin administration. The hemoglobin (HgB) was subsequently administered as an intravenous bolus. The blood pressure drop was abrogated by this administration and the hypotension was partially reversed. This effect lasted approximately 45 minutes before the blood pressure decline resumed. The subsequent decline was only slightly influenced by the administration of 5 grams of bovine serum albumin (BSA). On repetition of this experiment, substantially the same results were obtained.

EXAMPLE 2

Binding of NO by Myoglobin

Nitric oxide formation by endothelial cell cytosol was measured by a novel kinetic 96-well microplate assay. The assay is based on the capture of NO by $Fe^{2+}$-myoglobin (Mb) which is subsequently oxidized to $Fe^{3+}$-myoglobin. The process of heme oxidation was continuously measured in a kinetic microplate reader (Molecular Devices, Menlo Park Calif.) as the rate of change in $OD_{405}$–$OD_{650}$. Data points were collected from all 96 wells every 16 sec. for 30 minutes at 25° C. with shaking prior to each OD measurement. The slope of the best fit regression line (OD/min) was used to calculate the rate of NO-synthesis. OD/min measurements were converted to pmoles NO/min by dividing by the increase in OD405–OD$_{650}$ measured upon complete oxidation of 1 pmole of reduced Mb with a 10-fold molar excess of potassium ferricyanide. Under the conditions employed, the efficiency of NO capture by Mb approached 100%; neither doubling nor halving the concentration of Mb influenced the Mb oxidation rate. All samples contained 5–30 µl of endothelial cell cytosol (1–6 mg protein/ml) and final concentrations of 5 µM Mb, 500 µM L-arginine, 500 µM NADPH and 80 Mm TRIS, pH 7.6.

$Fe^{2+}$-Myoglobin Preparation: 2 mM myoglobin (from horse skeletal muscle, Sigma) was reduced with a sodium dithionite and immediately applied to a Sephadex G-25 column, followed by elution with 50 Mm TRIS buffer, pH 7.6. Mb was aliquoted and stored at −70° C. for up to 2 months prior to use. The usefulness of this iron hemoprotein for nitric oxide removal is thus clearly shown.

EXAMPLE 3

HEMALBUMIN (heme-albumin)

The oxidation state of the iron in hemalbumin may vary so that it is in fact methemalbumin, wholly or partially. Often in the literature "hemalbumin" is more precisely, methemalbumin. It is clear that the heme binding site in albumin is "designed" to bind heme with high affinity but not to insert that heme in a globin-like heme pocket. Along the lines of nitric oxide sequestration, several things should be noted.

Figure 2:
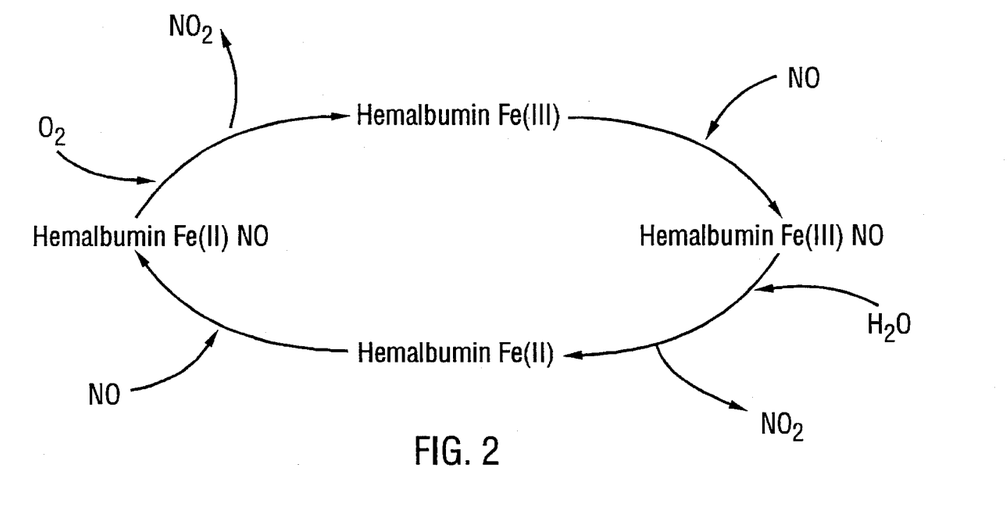
FIG. 2 schematically illustrates a redox cycle involving hemalbumin and nitric oxide.

The first is a catalytic cycle of nitric oxide turnover. Based on a present inventor's discovery of CO-driven reduction (Bickar, et al. JBC 259:10777–10783 (1984)), it appears certain that NO binds to ferric or methemalbumin. The affinity can easily be determined. The bound NO can then drive reduction of the ferric iron to ferrous with concomitant production of $NO_2$. Any excess NO will then bind, with extremely high affinity, to the ferrous hemalbumin. Because the heme binding site of albumin is not globin-like, the nitrosyl ferrous hemalbumin will be quite susceptible to autoxidation (if oxygen or other oxidants are present). This would then lead to the production of methemalbumin again and, hence, the beginning of a catalytic cycle. (See FIG. 2).

With respect to sequestration of nitric oxide, the binding constant of NO to ferrous hemalbumin is several orders of magnitude higher than that of methemalbumin (ferric hemalbumin). Accordingly, the preparation of a stable ferrous hemalbumin will be useful and potentially even better as an NO scavenger in the blood stream. Such a stable preparation, introduced into the venous system would probably remain stable for a considerable length of time, allowing for high-affinity binding of nitric oxide.

A series of reductants were tested for effectiveness in methemalbumin reduction. Methemalbumin was prepared by adding hemin chloride to a solution of human serum albumin (HSA). Hemin chloride was first dissolved in a minimal volume of a solution of dimethyl sulfoxide/0.15M phosphate-buffered saline pH 7.4 (3:5, v/v) containing 1/60th volume of 1N NaOH. A 25% solution of HSA Albumin-USP 25%; Cutter Pharmaceuticals, Cutter, U.S.A.) was then added by vigorous vortex mixing. The resultant deep amber (but crystal clear) solution of methemalbumin was used without further purification.

Iron picket fence porphyrin (Porphyrin Products, Provo, Utah) was dissolved in the same solvent used for hemin chloride. Then, HSA was again added as described above and the preparation was used without further purification. Canine (RBC's) were obtained from blood collected from the saphenous veins into heparin-containing tubes. RBCs from 5 ml of whole blood ($6\times10^9$ RBCs/ml) were collected by centrifugation, washed twice in phosphate buffered saline, pH 7.4 (PBS), and resuspended in 200 µl PBS by vortex mixing. The intact RBC suspension was further diluted with either 2.5 ml PBS (unlysed cells) or 2.5 ml of distilled water (lysed RBCs).

Methemalbumin, diluted with phosphate-buffered saline (PBS) at pH 7.4, was put into five stoppered cuvettes (2.5 ml each with $A_{500}$ of about 0.8). One was scanned, and dithionite was added to it. The other four were degassed and flushed with nitrogen to remove all oxygen. To the first of these was added 0.02M ascorbate that had been degassed and bubbled with nitrogen. The second was injected with 0.02M dithiothreitol that had also been degassed and bubbled with nitrogen. The third received degassed and nitrogen-bubbled reduced glutathione at the same concentration. The fourth sample was injected with 100 µl of NO. The syringes were flushed extensively with nitrogen or NO.

Each sample was scanned at various time intervals. After about 3 hours the samples were photographed, during which time they were under bright light for about 4 minutes. About 45 minutes later they were bubbled with CO, equilibrated about 20 minutes and rescanned. Absorbance spectra from 400 to 700 millimicrons were measured and used to monitor ferrous hemalbumin content. These experiments show that 0.02M dithiothreitol can reduce methemalbumin and that this reduced molecule can bind CO. Sodium dithionite can also reduce methemalbumin ut neither 0.02N ascorbate or 0.02M reduced glutathione can. Dithionite slowly reduces the methemalbumin. Neither ascorbate nor reduced glutathione appear to be effective. Dithiothreitol, however, effectively reduced the molecule. Sephadex G-25 or other means of removing excess reductant from reduced ferrous hemalbumin (under low oxygen conditions) will be used to determine whether it can be stably stored in a vial or ampule. The present inventors have previously discovered that NADPH can reduce ferric hemoglobin (via a superoxide-mediated pathway) and, of course, cytochrome $b_5$ (methemoglobin reductase) also works. These are systems should also be usable to reduce methemalbumin. Another reduction method should be to reduce with dithionite to the extent that that can be done, make the carbon monoxide derivative and then remove the carbon monoxide. Additionally, the albumin can be loaded with reduced-CO heme, then dialyzed and subsequently the CO can be removed. The ultimate object is to produce a stable ferrous hemalbumin suitable for transmission and usage.

EXAMPLE 4

HEMALBUMIN (heme-albumin) FOR ALLEVIATION OF HYPOTENSION

Example 1 describes the use of hemoglobin as a treatment for systemic hypotension induced by cytokines or endotoxins. The mechanism of action appears related to the formation of nitric oxide-hemoglobin complexes which neutralize the endothelium-derived relaxing factor activity of nitric oxide. This Example details the use of an artificially modified albumin protein with heme which is used to scavenge nitric oxide.

With respect to hemalbumin preparation and storage, the following "recipe" was used. Ingredients: 100 ml 25% human serum albumin solution; 231mg hemanchloride; 8 ml 3:5 (V/V) dimethylsulfoxide solution (made by mixing 3 ml 100% dimethylsulfoxide and 5ml phosphate buffered saline, pH 7.4); and a 1/60 solution of 1N NaOH.

The hemalbumin was made as follows. The 3:5 DMSO solution (2.7 ml) is pipetted into a small beaker and a 300 μl volume of 1N NaOH (1:10 dilution) was added. This solvent was then added to the small beaker containing 231 mg of heme. This was stirred until the heme dissolved. The solubilized heme was then added by a syringe to a vial containing 100ml of 25% human serum albumin. The albumin vial was mixed by a vortex mixing during the heme addition. The amber, crystal-clear solution was stored at 4° C.

Figure 3A:
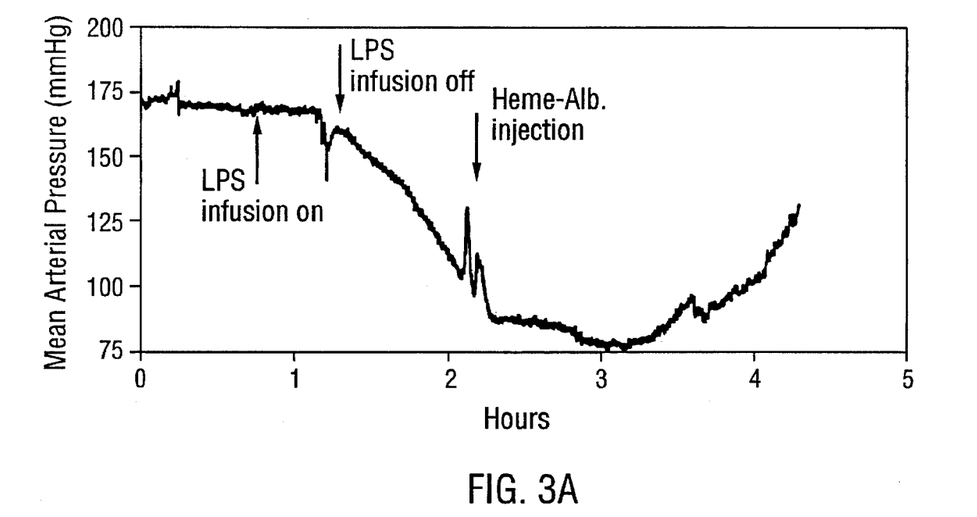
FIG. 3A shows the effects of lipopolysaccharide (LPS) and hemalbumin on a dog's mean arterial blood pressure.
Figure 3B:
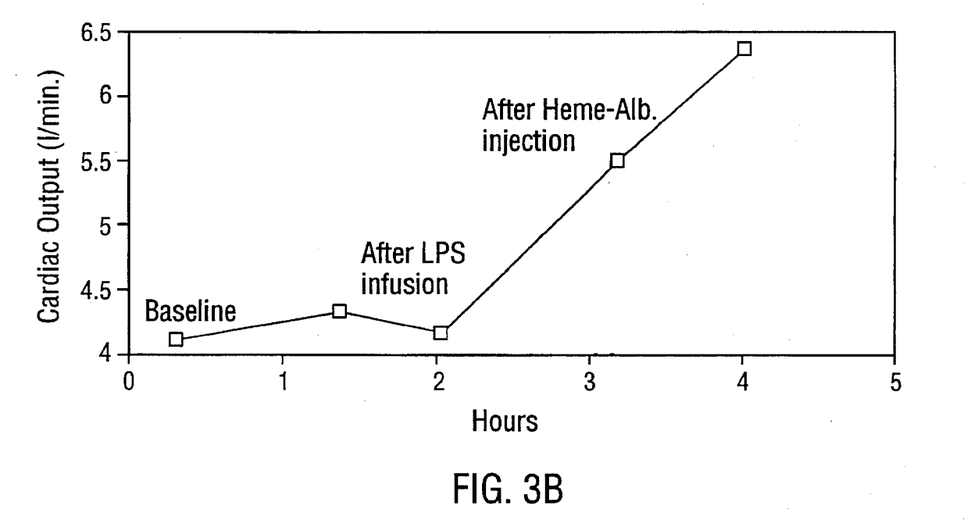
FIG. 3B shows the effects of lipopolysaccharide (LPS) and hemalbumin on a dog's cardiac output.
Figure 3C:
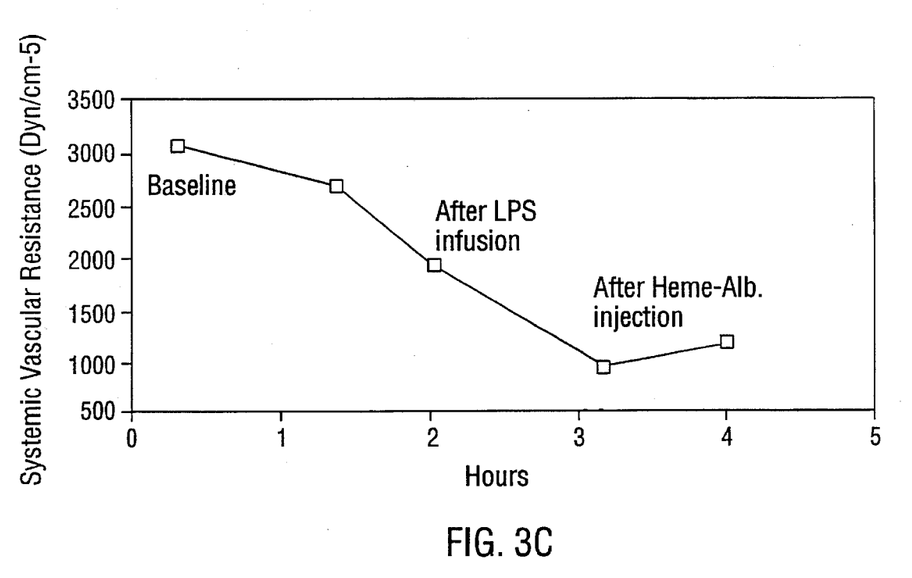
FIG. 3C shows the effects of lipopolysaccharide (LPS) and hemalbumin on a dog's systemic vascular resistance.

The hemalbumin acts by binding and/or converting nitric oxide to nitrates or nitrites and, therefore, inhibiting the vasodilatory effects of nitric oxide. The effects of hemalbumin in a dog treated with endotoxin is detailed in FIGS. 3A–3C. Endotoxin was administered at 200 μg/kg as an i.v. infusion over 20 minutes. After administration of the endotoxin was complete, the animal developed progressive hypotension which is noted by a decline in the mean arterial blood pressure detailed in FIG. 3A. The administration of hemalbumin (25 g of albumin in 50 cc) (2nd arrow) abrogated the fall in blood pressure due to endotoxin and stabilized the blood pressure. This stabilization of blood pressure was not observed with the administration of free albumin. FIGS. 3B and 3C respectively describe endotoxin (LPS) and hemalbumin effects on cardiac output and systemic vascular resistance.

Various references are cited above, the disclosures of which are incorporated in pertinent part by reference herein for the reasons cited.

The invention described and claimed herein is not to be limited in scope by the specific embodiments disclosed, since these embodiments are intended as illustrations of several aspects of the invention. Equivalent embodiments are intended to be within the scope of this invention. Indeed various modifications of the invention in addition to those shown and described herein will become apparent to those skilled in the art from the foregoing description. Such modifications are also intended to fall within the scope of the appended claims.

A variety of other hemoproteins or hemopeptides besides those specifically described herein are usable. The only requirement is that they effectively bind and/or catalyze nitric oxide oxidation. The methodology of Example 2 may be used to determine specific workable hemoproteins. Likewise, transition metals other than iron may be complexed in heme (metallohemoprotein) and analogously tested to determine effective complexes for nitric oxide removal. With respect to other transition metals and rationale for their NO binding activity, see Cotten, F. A., and Wilkinson, G., ADVANCED INORGANIC CHEMISTRY, A COMPREHENSIVE TEXT. Interscience Publishers, John Wiley and Sons, Inc., 1972, Chapter 22, "Complexes of π-Acceptor (π-Acid) Ligands, pages 682–727. Of course, any pharmaceutically acceptable salt forms of the hemoproteins may also be used as desired.

What is claimed is:

1. A method for treating a deleterious physiological effect in an animal caused by nitric oxide synthesis induced by a biological response modifier, the method comprising administering a therapeutically effective amount of a transition metal-hemoprotein selected from the group consisting of myoglobin, hemalbumin or methemalbumin to said animal.

2. A method for treatment of nitric oxide-induced hypotension comprising administering a therapeutically effective amount of a metallohemoprotein binding nitric oxide or catalyzing nitric oxide oxidation selected from the group consisting of myoglobin, hemalbumin or methemalbumin.

3. The method of claim 1 or 2 wherein the amount is from 0.1 to 10 g/kg body weight.

4. The method of claim 1 wherein the administering is intravascular.

5. The method of claim 1 wherein the deleterious physiological effect is systemic hypotension.

6. A method for treatment of an animal for systemic hypotension caused by nitric oxide comprising administering a therapeutically effective amount of myoglobin, hemalbumin or methemalbumin.

7. The method of claim 6 wherein the nitric oxide is induced by a cytokine.

8. The method according to claim 7 wherein the cytokine is tumor necrosis factor, interleukin-1, or interleukin-2.

9. A method for the treatment of an animal for systemic hypotension induced by endotoxin comprising administering a therapeutically effective amount of myoglobin, hemalbumin or methemalbumin.

10. A method for the treatment of septic shock in a patient comprising administering a therapeutically effective amount of a transition metal hemoprotein selected from the group consisting of myoglobin, hemalbumin or methemalbumin.

11. A method for the treatment of septic shock in a patient comprising administering a therapeutically effective amount of hemalbumin.

12. A method for treatment of systemic hypotension in a patient caused by nitric oxide production induced by a cytokine selected from the group consisting of tumor necrosis factor, interleukin-1, and interleukin-2 comprising administering an amount of methemalbumin or hemalbumin sufficient to bind or oxidize substantially all nitric oxide produced.

13. The method of claim 6, 9 or 12 wherein the amount is from 0.1 to 10 g/kg body weight.

14. The method of claim 6, 9 or 12 wherein the administering is intravascular.

* * * * *